United States Patent
Syed

(10) Patent No.: US 11,426,344 B2
(45) Date of Patent: Aug. 30, 2022

(54) METHODS AND COMPOSITIONS FOR STRAIGHTENING HAIR

(71) Applicant: SALON COMMODITIES, INC., Melrose Park, IL (US)

(72) Inventor: Ali Naqi Syed, Oak Brook, IL (US)

(73) Assignee: Salon Commodities, Inc., Melrose Park, IL (US)

( * ) Notice: Subject to any disclaimer, the term of this patent is extended or adjusted under 35 U.S.C. 154(b) by 133 days.

(21) Appl. No.: 16/497,639

(22) PCT Filed: Mar. 22, 2018

(86) PCT No.: PCT/US2018/023818
§ 371 (c)(1),
(2) Date: Sep. 25, 2019

(87) PCT Pub. No.: WO2018/183087
PCT Pub. Date: Oct. 4, 2018

(65) Prior Publication Data
US 2020/0022903 A1   Jan. 23, 2020

Related U.S. Application Data

(60) Provisional application No. 62/476,743, filed on Mar. 25, 2017.

(51) Int. Cl.
| | |
|---|---|
| A61Q 5/06 | (2006.01) |
| A61K 8/898 | (2006.01) |
| A61K 8/36 | (2006.01) |
| C08G 77/04 | (2006.01) |
| C08G 77/14 | (2006.01) |
| C08G 77/26 | (2006.01) |

(52) U.S. Cl.
CPC ............ *A61K 8/898* (2013.01); *A61K 8/36* (2013.01); *A61Q 5/06* (2013.01); *C08G 77/045* (2013.01); *C08G 77/14* (2013.01); *C08G 77/26* (2013.01); *A61K 2800/20* (2013.01); *C08G 2261/142* (2013.01); *C08G 2261/143* (2013.01); *C08G 2261/1644* (2013.01)

(58) Field of Classification Search
None
See application file for complete search history.

(56) References Cited

U.S. PATENT DOCUMENTS

| | | | |
|---|---|---|---|
| 5,312,968 A | 5/1994 | O'Lenick, Jr. et al. | |
| 5,488,121 A | 1/1996 | O'Lenick, Jr. | |
| 5,989,533 A | 11/1999 | Deegan et al. | |
| 6,175,028 B1 | 1/2001 | O'Lenick, Jr. | |
| 2004/0158938 A1 | 8/2004 | Geary et al. | |
| 2006/0013795 A1 | 1/2006 | Kawata et al. | |
| 2006/0018867 A1 | 1/2006 | Kawasaki et al. | |
| 2013/0058880 A1 | 3/2013 | Dong | |
| 2015/0096584 A1 | 4/2015 | Washington et al. | |
| 2015/0305469 A1 | 10/2015 | Paul | |
| 2019/0029945 A1 | 1/2019 | Syed et al. | |

FOREIGN PATENT DOCUMENTS

| | | | |
|---|---|---|---|
| EP | 2 538 916 A2 | 1/2013 | |
| WO | WO 2009/061360 A1 | 5/2009 | |
| WO | WO-2014068101 A2 * | 5/2014 | ............... A61Q 5/04 |
| WO | WO 2015/155047 A1 | 10/2015 | |
| WO | WO 2017/124061 A1 | 7/2017 | |

OTHER PUBLICATIONS

Pubchem, Substance Record for SID 272710350, Available Date: Dec. 11, 2015 [retrieved on Jun. 21, 2018]. Retrieved from the Internet: <URL: https://pubchem.ncbi.nlm.nih.gov/substance/272710350>.
Pubchem, Substance Record for SID 252226016, Available Date: Sep. 1, 2015 [retrieved on Jun. 21, 2018]. Retrieved from the Internet: <URL: https://pubchem.ncbi.nlm.nih.gov/substance/252226016>.
United States Patent and Trademark Office, International Search Report in International Application No. PCT/US2018/023818 (dated Jul. 11, 2018).
United States Patent and Trademark Office, Written Opinion in International Application No. PCT/US2018/023818 (dated Jul. 11, 2018).
International Bureau of WIPO, International Preliminary Report on Patentability in International Application No. PCT/US2018/023818 (dated Oct. 10, 2019).
European Patent Office, Extended European Search Report in European Patent Application No. 18775902.2 (dated Dec. 16, 2020).
U.S. Appl. No. 16/069,138, filed Jul. 10, 2018.

* cited by examiner

*Primary Examiner* — Jyothsna A Venkat
(74) *Attorney, Agent, or Firm* — Leydig, Voit & Mayer, Ltd.

(57) ABSTRACT

Provided are methods for straightening hair, which comprise contacting the hair with a hair straightening agent and one or more aminosilicones, and, optionally, one or more epoxysilicones. Also provided are compositions, which include a carrier, a hair straightening agent, and an effective amount of one or more aminosilicones, and, optionally, one or more epoxysilicones. Additionally provided are products, which include one or more hair straightening agents, an effective amount of one or more aminosilicones, and instructions for applying the hair straightening agent(s) and aminosilicone(s) to the hair. The products of the invention may optionally include an effective amount of one or more epoxysilicones and instructions for applying the epoxysilicone(s) to the hair.

8 Claims, 1 Drawing Sheet

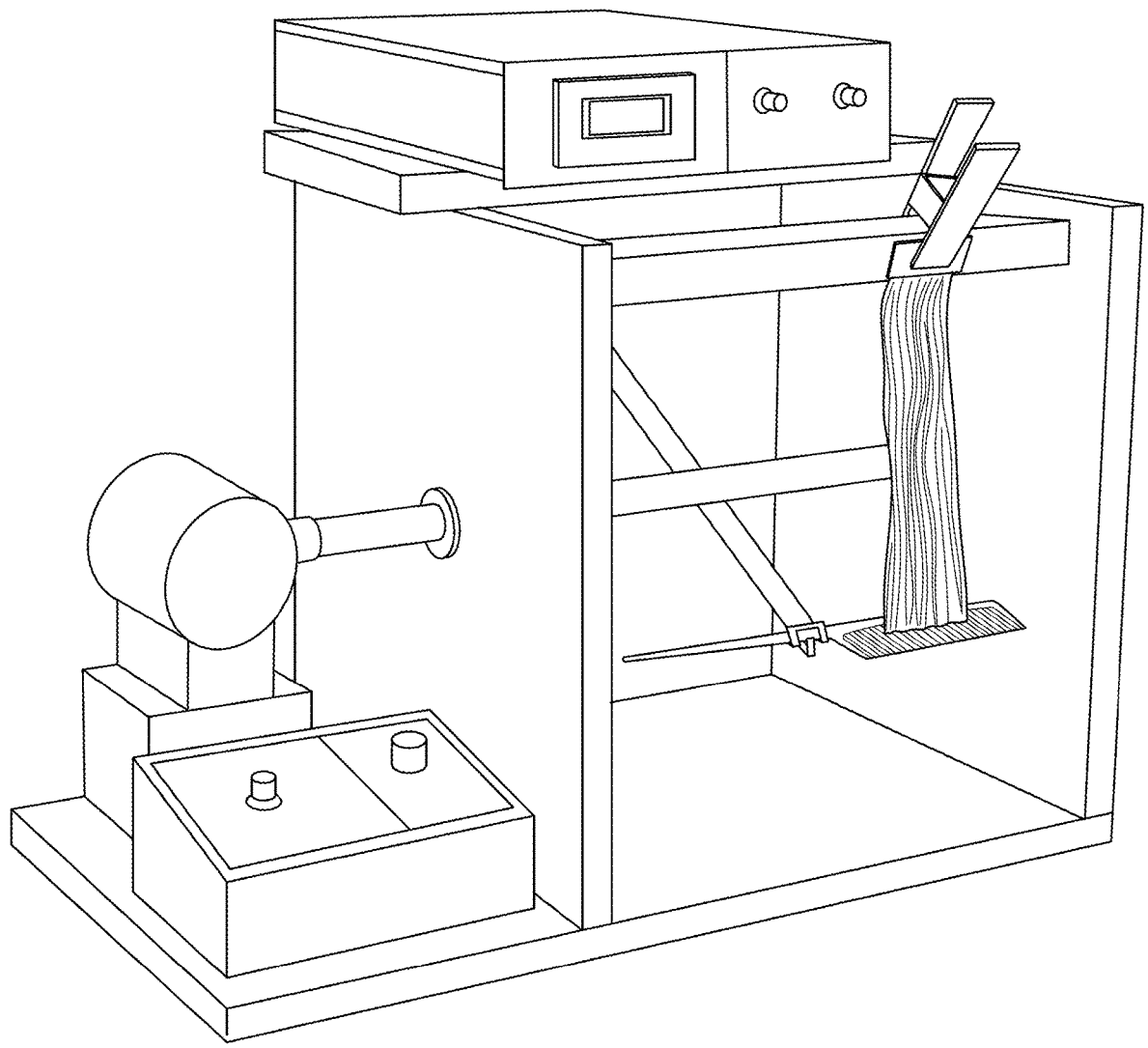

METHODS AND COMPOSITIONS FOR STRAIGHTENING HAIR

CROSS-REFERENCE TO RELATED APPLICATIONS

This patent application is the U.S. national stage of International Application No. PCT/US2018/023818, filed on Mar. 22, 2018, which claims the benefit of U.S. Provisional Patent Application No. 62/476,743, filed Mar. 25, 2017, the disclosures of which are incorporated herein by reference in their entireties for all purposes.

BACKGROUND OF THE INVENTION

Wavy, curly and super curly hair is found among many races in the world. Slightly wavy and wavy hair is very prevalent among people of Central American, Middle Eastern, Southern European, and South East Asian descent, as well as certain Caucasian races in North America. Super curly hair is often found among people of African American, Puerto Rican, Cuban, and Caribbean (including Dominican Republic) descent.

It is well-known that wavy, curly and super curly hair is difficult to comb, which presents unique problems in the context of styling. Usually, the wavy, curly and super curly hair assemblies carry a large volume and, especially under humid conditions, present difficulties in the context of maintaining a particular style. Consumers, for example, may straighten their hair with either heat appliances, such as blow driers and flat irons, or may attempt to "permanently" straighten their hair with chemically reactive products such as hair relaxers based upon sodium/lithium hydroxide, guanidine hydroxide, or ammonium thioglycolate. Super curly and coily hair responds well to hair relaxers based upon sodium hydroxide or guanidine hydroxide, whereas somewhat wavy and wavy hair can be very resistant to relaxer processes, and some of the waves can even reappear one day after treatment.

As an attempt to achieve permanent straightening, hair stylists in Brazil devised formulations that contained formaldehyde in a liquid or lotion vehicle. These concoctions were applied to hair, and the hair was blow dried and flat ironed while the formaldehyde product was on the hair. After flat ironing hair, the hair was styled with usual styling products. The hair felt very silky, straight and shiny. This technique was called Brazilian Keratin Treatment (BKT) or Brazilian Smoothing Treatment, and became very popular in Brazil and consequently in many parts of the world including USA and Europe. The major drawbacks of formaldehyde-based products are their health risks and Regulatory restrictions. The United States Food and Drug Administration (FDA) allows the use of formaldehyde as a preservative in cosmetic products and the usage level is restricted to 0.20% active level. The use of formaldehyde as a straightening ingredient further poses risk to the health of the operator (hairstylist) and the customer through formaldehyde fumes that are given off during the blow-drying process while the product containing high levels of formaldehyde is in the customer's hair. The heat of the blow dryer spreads the formaldehyde fumes throughout the hair salon, subjecting the salon environment to formaldehyde exposure.

More recently, Glyoxylic Acid and a derivative of Glyoxylic Acid known as Oxoacetamido Carbocysteine (or Oxoacetamide) have been utilized as a substitute for formaldehyde with reasonable success. However, there are still certain drawbacks associated with Glyoxylic Acid and Oxoacetamido Carbocysteine. For effective straightening, the concentration of Glyoxylic Acid or Oxoacetamide Carbocysteine used is in the range of 15.0-20.0%% or greater, which is damaging to hair. Also, since the pH of these two ingredients is very low, that is, around 1.0, they develop sulfurous odor in the wet hair. In addition, after treatment, the hair fibers develop excessive static charge, making the hair more difficult to style due to "fly-aways." The use of high glyoxylic acid concentrations makes the hair and scalp dry, such that the scalp loses its moisture and the transepidermal water reduces significantly, leaving the stratum cornium vulnerable to further damage. Further, hair fibers are not as soft and shiny after treatment with Glyoxylic Acid or Oxoacetamide Carbocysteine. Moreover, the use of high glyoxylic acid concentrations can result in significant color loss of color treated hair, creating an undesirable appearance.

Accordingly, there is a need for improved methods, compositions and products, which straighten hair effectively but with reduced negative effects, e.g., undesirable odor, texture, and/or static charge. The present invention provides such methods, compositions and products.

BRIEF SUMMARY OF THE INVENTION

The present invention provides method for straightening hair, which method includes contacting the hair with a hair straightening agent and an effective amount of an aminosilicone. Suitable aminosilicones include compounds of formula (I):

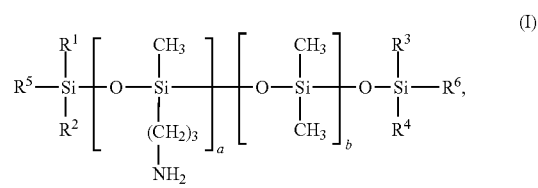

wherein $R^1$-$R^4$ are methyl; $R^5$ and $R^6$ are the same or different and each is $C_{1-26}$ alkyl or a substituent of the formula $(CH_2)_3$—$NH_2$; a is from 0-20; and b is from 0-300; provided that when a is 0, then at least one of $R^5$ and $R^6$ is $(CH_2)_3$—$NH_2$.

Exemplary compounds of formula (I) include compounds of the formula:

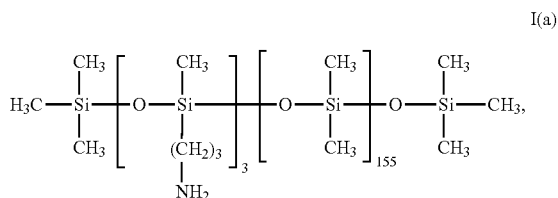

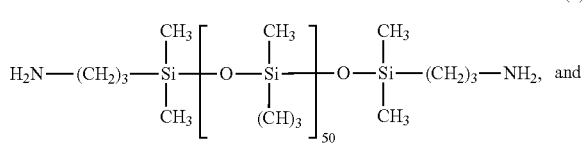

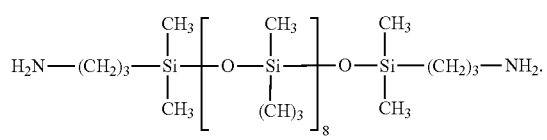

The method of the invention optionally includes contacting the hair with an effective amount of an epoxysilicone. Examples of epoxysilicones that may be used in accordance with the present invention are described in PCT/US2017/013612 (entitled "Methods and Compositions for Treating Damaged Hair," and claiming priority to U.S. Patent Application No. 62/279,438), incorporated herein in its entirety by reference. Examples of suitable epoxysilicones include epoxysilicones of the formula:

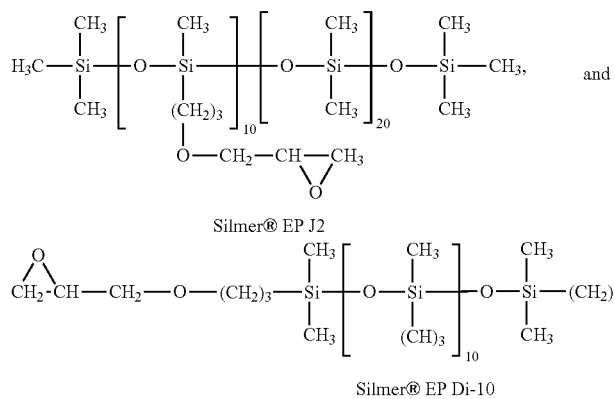

The epoxysilicone may be applied to the hair before the hair straightening agent is applied to the hair. Alternatively or additionally, in accordance with the present invention, the epoxysilicone and hair straightening agent may be applied to the hair concurrently, e.g., at the same time, or together as a combination or mixture.

The invention also provides a composition, which includes a carrier, a hair straightening agent, and an effective amount of a compound of formula (I), as described herein. The composition of the present invention may optionally include an effective amount of an epoxysilicone, as described herein.

The invention further provides a product, which includes a hair straightening agent, an effective amount of a compound of formula (I), and instructions for applying the hair straightening agent and compound of formula (I) to the hair, as described herein. The product of the invention may optionally include an effective amount of an epoxysilicone, and instructions for applying the epoxysilicone to the hair, as described herein.

BRIEF DESCRIPTION OF THE SEVERAL VIEWS OF THE DRAWING(S)

FIG. 1 depicts a charge measuring device.

DETAILED DESCRIPTION OF THE INVENTION

The present invention is predicated on the surprising and unexpected discovery that certain aminosilicone compounds can improve efficacy of hair straightening procedures, which utilize restructuring agents that can be damaging to the hair, e.g., aldehyde-containing hair straightening agents, e.g., glyoxylic acid, derivatives, and salts thereof. The present invention is also predicated on the surprising and unexpected discovery that certain epoxysilicone compounds can further augment the efficacy of the hair-straightening process of the invention. The present invention thus allows for a significant reduction in the amount of hair straightening agent needed to straighten hair, but without loss of hair straightening efficacy. This is especially advantageous in the context of procedures that utilize hair straightening agents that are damaging to the hair, e.g., glyoxylic acid.

In one embodiment, the present invention provides method for straightening hair, which method includes contacting the hair with a hair straightening agent and an effective amount of a compound of formula (I):

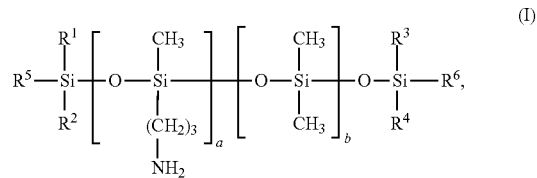

wherein $R^1$-$R^4$ are methyl; $R^5$ and $R^6$ are the same or different and each is $C_{1-26}$ alkyl or a substituent of the formula $(CH_2)_3$—$NH_2$; a is from 0-20; and b is from 0-300; provided that when a is 0, then at least one of $R^5$ and $R^6$ is $(CH_2)_3$—$NH_2$.

Any suitable combination of a, b, $R^5$ and $R^6$ may be employed in accordance with the present invention. In one embodiment, each of $R^5$ and $R^6$ of formula (I) are methyl, in which case a is preferably at least 1. In another embodiment, each of $R^5$ and $R^6$ are a substituent of the formula —$(CH_2)_3$—$NH_2$, in which case a is preferably 0. In some embodiments, $R^5$ and $R^6$ are methyl, and: a is at least 1, and b is at least 1; a is at least 1, and b is from 100-200; a is from 1-10, and b is at least 1; a is from 1-10, and b is from 100-300; a is from 1-10, and b is from 100-200; a is from 1-5, and b is from 100-300; and a is from 1-5, and b is from 100-200. In other embodiments, $R^5$ and $R^6$ are $(CH_2)_3$—$NH_2$, and: a is 0, and b is at least 1; a is 0, and b is from 1-100; a is 0, and b is from 1-50; and a is 0, and b is from 1-10. Suitable compounds of formula (I) include compounds of the formula:

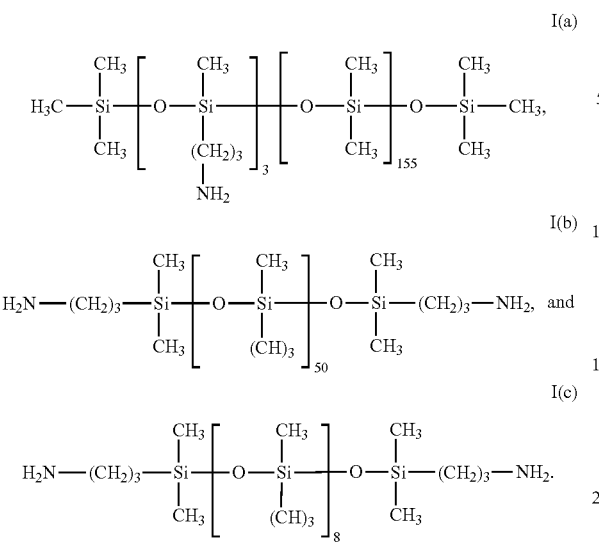

Certain compounds represented by formulae (I) may be obtained commercially, e.g., from Siltech LLC of Lawrenceville, Ga. For example, the compound represented by formula (Ia) is currently marketed by Siltech LLC under the trade name Silmer® NH C$_{50}$. The compound represented by formula (Ib) is currently marketed by Silmer® NLLC under the trade name Silmer® NH Di-50. The compound represented by formula (Ic) is currently marketed by Siltech LLC under the trade name Silmer® NH Di-8. Other suitable aminosilicones also may be obtained from Siltech LLC.

The hair straightening agent used in the method of invention can include aldehyde-based hair straightening agents. Suitable aldehyde-based hair straightening agents can include, for example, glyoxylic acid, one or more glyoxylic acid derivatives, and/or one or more salts of glyoxylic acid. In some embodiments, the hair straightening agent includes glyoxylic acid or a thereof, and/or glyoxyloyl carbocysteine (oxoacetamido carbocysteine) or a salt thereof. In some applications of the present invention, the hair straightening agent includes glyoxylic acid or a salt thereof. When glyoxylic acid or salt thereof is used as a hair straightening agent in the method of the present invention, the glyoxylic acid concentration is preferably below the glyoxylic acid concentration conventionally used in hair-straightening procedures, or preferably less than 15%. In some embodiments of the present invention, glyoxylic acid or salt thereof is used at a glyoxylic acid concentration of preferably about 10% or less.

In accordance with the present invention, the compound of formula (I) may be applied to the hair before the hair straightening agent is applied to the hair. Alternatively or additionally, in accordance with the present invention the compound of formula (I) and hair straightening agent may be applied to the hair concurrently, e.g., at the same time, or together as a combination or mixture.

The method of the present invention further includes optionally contacting the hair with an effective amount of an epoxysilicone. Examples of epoxysilicones that may be used in accordance with the present invention are described in PCT/US2017/013612, which is incorporated herein in its entirety by reference. Suitable epoxysilicones include, e.g., epoxysilicones of the formula:

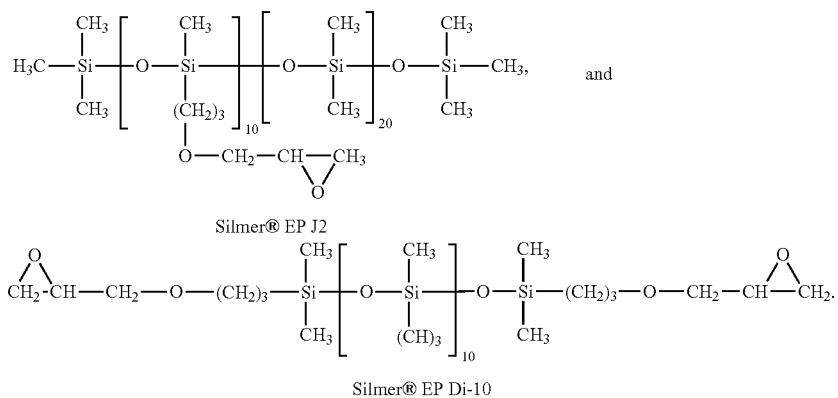

Both Silmer® EP J2 and Silmer® EP Di-10 are currently marketed by Siltech LLC. Other suitable epoxysilicones also may be obtained from Siltech LLC.

In accordance with the present invention, the epoxysilicone may be applied to the hair before the hair straightening agent is applied to the hair. Alternatively or additionally, in accordance with the present invention, the epoxysilicone and hair straightening agent may be applied to the hair concurrently, e.g., at the same time, or together as a combination or mixture.

The invention also provides a composition, which includes a carrier, a hair straightening agent, and an effective amount of a compound of formula (I) as defined herein. The hair straightening agent used in the composition of invention is preferably an aldehyde-based hair straightening agent. Suitable aldehyde-based hair straightening agents can include, for example, glyoxylic acid, one or more glyoxylic acid derivatives, and/or one or more salts of glyoxylic acid. In some compositions of the invention, the hair straightening agent includes glyoxylic acid or a thereof, and/or glyoxyloyl carbocysteine (oxoacetamido carbocysteine) or a salt thereof. In some cases, the hair straightening agent includes glyoxylic acid or a salt thereof. When glyoxylic acid or salt thereof is used as a hair straightening agent in the composition of the present invention, the glyoxylic acid concentration is preferably below the glyoxylic acid concentration conventionally used in hair-straightening procedures, or preferably less than 15%. In some embodiments, glyoxylic acid or salt thereof is used at a glyoxylic acid concentration of preferably about 10% or less.

The composition of the present invention may optionally include an effective amount of an epoxysilicone. Examples of epoxysilicones that may be used in accordance with the present invention are described in PCT/US2017/013612, which is incorporated herein in its entirety by reference, including Silmer® EP J2 and Silmer® EP Di-10, which are currently available from Siltech LLC.

The carrier used in the composition of the present invention is preferably an aqueous carrier. It will be appreciated that the water solubility of the compound of formula (I) may impact how one of ordinary skill in the art might approach formulating the compound in an aqueous liquid. However, the compound of formula (I) need not be water soluble in order to be formulated in an aqueous vehicle, and need not be water soluble in order to be effective for purposes of treating hair damage. As such, the compound of formula (I) may be water soluble, sparingly soluble in water, or water insoluble and still be effective for purposes of the present invention.

When the compound of formula (I) is water soluble, the composition of the present invention may be formulated as an aqueous solution. When the compound of formula (I) is insoluble (or only sparingly soluble) in water, the compound of formula (I) is preferably formulated as an aqueous emulsion. Water insoluble compounds of formula (I) may be formulated as aqueous emulsions by any suitable method, including methods that are known in the art for formulating aqueous emulsions of water insoluble organic compounds. Suitable emulsions may include one or more emulsifiers, which are effective in stabilizing aqueous emulsions of the compound of formula (I). Suitable emulsifiers may include, for example, emulsifying phosphate esters, e.g., dicetyl phosphate and ceteth-10 phosphate, polyoxyalkylene sorbitan esters, e.g., polysorbates, e.g., polysorbate 20, polysorbate 40, polysorbate 60, and the like, and combinations thereof. Examples of suitable methods, conditions, concentrations, and systems for preparing aqueous emulsions are described in PCT/US2017/013612.

The compounds represented by formulae I(a)-I(c) are preferably formulated as aqueous emulsions. The epoxysilicones optionally used in accordance with the present invention also may be formulated as emulsions, e.g., as taught by PCT/US2017/013612. When Silmer® EP J2 and/or Silmer® EP Di-10 are used, for example, they are preferably formulated as aqueous emulsions, e.g., as taught by PCT/US2017/013612.

The invention further includes a product, which includes a hair straightening agent, an effective amount of a compound of formula (I) as defined herein, and instructions for applying the hair straightening agent and compound of formula (I) to the hair. The hair straightening agent used in the product of the invention can include an aldehyde-containing hair straightening agent as described herein. The hair straightening agent used in the product of the invention may be included at concentrations as described herein. Suitable aldehyde-based hair straightening agents can include, for example, glyoxylic acid, one or more glyoxylic acid derivatives, and/or one or more salts of glyoxylic acid. In some compositions of the invention, the hair straightening agent includes glyoxylic acid or a thereof, and/or glyoxyloyl carbocysteine (oxoacetamido carbocysteine) or a salt thereof. In some cases, the hair straightening agent includes glyoxylic acid or a salt thereof. When glyoxylic acid or salt thereof is used as a hair straightening agent in the composition of the present invention, the glyoxylic acid concentration is preferably below the glyoxylic acid concentration conventionally used in hair-straightening procedures, or preferably less than 15%. In some embodiments, glyoxylic acid or salt thereof is used at a glyoxylic acid concentration of preferably about 10% or less.

The product of the present invention may optionally include an effective amount of an epoxysilicone, and instructions for applying the epoxysilicone to the hair. Examples of epoxysilicones that may be used in accordance with the present invention are described in PCT/US2017/013612 (incorporated herein in its entirety by reference). Examples of suitable epoxysilicones include Silmer® EP J2 and Silmer® EP Di-10, which are currently available from Siltech LLC. In one embodiment, the instructions for the product of the present invention recommend applying, or when followed result in the application of, the epoxysilicone to the hair before the hair straightening agent is applied to the hair. In another embodiment, the instructions for the product of the present invention recommend applying, or when followed result in the application of, the epoxysilicone and hair straightening to the hair concurrently.

The following examples further illustrate the invention but, of course, should not be construed as in any way limiting its scope.

Test Methods

Human subjects (patrons) were selected based upon their hair texture. Subjects with wavy, curly and super curly hair were chosen for the treatment. All subjects who participated in this particular study were women with wavy, curly, or super curly hair. Everyone was treated with a regimen of the products for straightening hair and data was collected.

The unit of analysis was an individual's head of hair. The head of hair of an individual was divided into two halves where hair was parted into two equal halves from the middle of the forehead to the middle of the back of the head. Two different products were applied to each half side, where one half side was a control product regimen and the other half side was treated with experimental product regimen (invention). Observations were made by the trained hair stylists in the art of hair straightening, and recorded on a given questionnaire.

Salon Questionnaire: The data was collected on the questionnaire about ease of product application, details of application, and then the attributes imparted to hair. These attributes were the degree of straightening, ease of combing during blow drying and flat ironing, static charge on the hair, the odor of the wet hair after treatment, the feel of the hair, shine imparted to the hair. In some cases, the responses of the individual models were also recorded. The questionnaire is attached in Exhibit A.

Intermittent Stress Relaxation (ISR): ISR testing was used to assess the internal chemical damage to hair via loss in elastic strength of wet hair fibers using TA's Dynamic Mechanical Analyzer model Q800 (TA Instruments, Inc., New Castle, Del.). The instrument consists of a drive motor that provides the static and dynamic or oscillatory force. The drive motor transmits force directly to the rectangular air-bearing slide that is also connected to the drive shaft and sample clamp. The compressed air supplied to the air bearings allows the slide to float. The distance or vertical movement of the air-bearing slide during testing is translated to the force required for that specific run. The optical encoder is used to measure the displacement during testing based on diffraction patterns of light through gratings (one stationary and one moveable). The furnace provides temperature control required during testing. Additional information concerning the ISR test can be found in PCT/US2017/013612, incorporated herein by reference in its entirety.

In this test, each single fiber (gauge length=14.82 mm) is mounted to the submersible fiber specimen clamp containing water. The fiber is stretched to a constant strain or 0.5% of its length (from 14.82 to 14.894 mm length) for 0.1 minute and allowed to recover for 0.9 minute. This process of imposing the strain and allowing it to recover is repeated for a total of 10 cycles. The force is expressed in grams while the area is expressed in denier (a textile terminology defined as weight in grams of 9,000 meters of yarns or fibers). The area of the hair specimen is measured using the LaserMike micrometer from Beta LaserMike, 8001 Technology Blvd, Dayton, Ohio, USA. The average area is recorded as (x+y)/2 where x is the minor axis and y the major axis. The amount of stress (g/denier) for each cycle is measured and recorded. The ratio of after to before treatment is calculated and used to assess the internal condition of hair fibers. An index of 1.0 indicates that there is no chemical damage done to the hair, while a value less than 1.0 suggests that fibers were internally damaged by the treatment.

Degree of Straightening:

The degree of straightening was compared after combing hair on each sides. If the hair was dead straight it was given a score of "5". Any score less than "5" was considered less straight. The subjective comparative evaluation of degree of straightness was made by the trained hair stylists in the art of hair straightening. The total scores of hair straightening for each group were compared using paired t-test.

Ease of Combing of Hair in Wet State:

The combing data was collected from the responses on the questionnaire by the hair stylists. The responses were analyzed using statistical methods for certain applications.

Comparison of Static Charge:

The comparison of static charge was collected by two methods. In a first method, responses of the hairstylists were collected on a 5-point Lickert scale and the data were analyzed statistically. In a second method, the hair was combed 20 times and the static charge was measured in Kilo Volts (KV), using charge measuring device (Trek Electrostatic Voltmeter Model 54) as shown in FIG. 1. The sensor is positioned next to the hair after it has been combed 20 times with the combing machine. The Trek Electrostatic voltmeter measures the charge on the hair in KV.

Comparison of Odor in Hair at Wet and Dry Stages:

The odor of the wet hair after treatment was determined by smelling the hair on both sides for the degree of foul/undesirable odor on a scale of 1 to 5, with a score of "1" being very undesirable or very foul odor and a score of "5" being a very pleasant/desirable odor.

Example 1

This example demonstrates compositions and methods of the present invention. Fiber Expander and Fiber Restructure compositions are described in Tables 1A and 1B.

TABLE 1A

Fiber Expander Formula

| Ingredients | Formula 1A-1 % |
|---|---|
| Deionized Water | 91.500 |
| Silmer ® NH Di-8 | 2.500 |
| Silmer ® EP Di-10 | 0 |
| Lipocol ® L-23 | 4.000 |
| Fragrance | 2.000 |

TABLE 1B

Fiber Restructure Formula

| Ingredients | Formula 1B-1 % | Formula 1B-2 % |
|---|---|---|
| Deionized Water | 69.500 | 72.00 |
| Lipocol ® L-23 | 6.000 | 6.000 |
| Fragrance | 2.000 | 2.000 |
| Glyoxylic Acid (50% active) | 22.500 | 20.00 | pH @ 25 C. = 1.81

Combination of Aminosilicone (Silmer® NH Di-8) and Glyoxylic Acid

A survey questionnaire was used to record the data by a trained hairstylist in hair smoothing treatments who performed the treatment at the time of products' application and process. In this preliminary study five individuals were treated with the system consisting of Fiber Expander with Diamines, Fiber Restructure with lower concentration of Glyoxylic Acid and a Thermal Protector.

A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill. 60160, USA. The application procedure is given below.

Application Procedure—Control

Divide hair into two halves.

Shampoo hair once using Uberliss® Hydrating Shampoo.

Apply Uberliss® Expander by using 15 to 20 strokes or 10 to 15 g per half head.

Dry hair to 80%.

Apply 20 to 25 g of Uberliss Fiber Restructure using a brush and combing through the hair.

Cover hair with plastic or Aluminum Cap. Leave product on hair for 20 minutes under dryer or steamer at high setting. Remove cap.

Apply ¼ tea spoon of Uberliss Nutritive Mask. Comb through using wide-tooth comb and cover hair with plastic or Aluminum Cap. Leave the product on for 10 minutes under the hooded dryer or steamer.

Rinse hair for 10 seconds with low pressure tepid water. The rinse water will be still whitish or like Coco-water.

Blow dry hair completely using paddle brush.

Divide hair into thin partings. Spray KeraCare® Thermal Wonder® Thermal Protector and flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Application Procedure—Invention

Divide hair into two halves.

Shampoo hair once using Uberliss® Hydrating Shampoo.

Apply Expander Formula 1A-1 (Table 1A) by using 15 to 20 strokes or 10 to 15 g per half head.

Dry hair to 80%.

Apply 20 to 25 g of Fiber Restructure Formula 1B-1 (Table 1B) using a brush and combing through the hair.

Cover hair with plastic or Aluminum Cap. Leave product on hair for 30 minutes under dryer or steamer at high setting. Remove cap.

Rinse hair for 10 seconds with low pressure tepid water. The rinse water will be still whitish or like Coco-water.

Blow dry hair completely using paddle brush.

Divide hair into thin partings. Spray KeraCare® Thermal Wonder® Thermal Protector and flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Comparison of Hair Straightening:

The wet hair straightening after treatment was compared, and the results are described in Table 1C.

TABLE 1C

Comparison of wet hair straightening between Uberliss Smoothing Treatment containing 15.00% Glyoxylic Acid and composition containing Silmer® NH Di-8 and 11.25% Glyxoylic Acid

| Model No. | Control System (Uberliss®) Straightening Score | Invention (Formulae 1A-1 and 1B-1) Straightening Score |
|---|---|---|
| 1 | 5.0 | 5.0 |
| 2 | 5.0 | 5.0 |
| 3 | 5.0 | 4.6 |
| 4 | 5.0 | 5.0 |
| 5 | 4.0 | 5.0 |

The control composition (Uberliss Fiber Restructure) contained 15.00% Glyxoylic Acid, whereas the composition of the invention (Formula 1A-1) contained only 11.25% Glyxoylic Acid. Nevertheless, the composition of the invention (containing 2.50% Silmer® NH Di-8) provided a straightening efficacy equal to that of the control group. This advantageously allows for a significant reduction in the amount of hair straightening agent (which can damage hair) without loss of efficacy.

Comparison of Combing

A comparison of ease of wet combing between control and experimental groups was conducted. The results are shown in Table 1D.

TABLE 1D

Comparison of wet hair combing of Uberliss Smoothing Treatment containing 15.00% Glyoxylic Acid and composition containing Silmer® NH Di-8 and 11.25% Glyxoylic Acid

| Model No. | Control System (Uberliss®) Ease of wet combing Score | Invention (Formulae 1A-1 and 1B-1) Ease of wet combing Score |
|---|---|---|
| 1 | 5.0 | 5.0 |
| 2 | 5.0 | 5.0 |
| 3 | 5.0 | 5.0 |

TABLE 1D-continued

Comparison of wet hair combing of Uberliss Smoothing Treatment containing 15.00% Glyoxylic Acid and composition containing Silmer® NH Di-8 and 11.25% Glyxoylic Acid

| Model No. | Control System (Uberliss®) Ease of wet combing Score | Invention (Formulae 1A-1 and 1B-1) Ease of wet combing Score |
|---|---|---|
| 4 | 3.0 | 5.0 |
| 5 | 5.0 | 5.0 |

The ease of wet combing observed after treatment with the composition of the invention was at least equivalent to that observed after treatment with control.

Comparison of Static Charge

Hair static charge between control and experimental groups was compared. The results are shown in Table 1E.

TABLE 1E

The comparison of the static charge between Uberliss Smoothing Treatment containing 15.00% Glyoxylic Acid and composition containing Silmer® NH Di-8 and 11.25% Glyxoylic Acid

| Model No. | Control System (Uberliss®) Degree of static charge | Invention (Formulae 1A-1 and 1B-1) Degree of static charge |
|---|---|---|
| 1 | 4.00 | 5.00 |
| 2 | 4.00 | 5.00 |
| 3 | 4.50 | 5.00 |
| 4 | 3.50 | 4.00 |
| 5 | 4.00 | 4.00 |

The static charge observed after treatment with the composition of the invention was significantly below the static charge observed after treatment with control. The reduction in static charge following treatment according to the invention demonstrates a substantial improvement over conventional treatment.

Comparison of Odor of Treated Wet Hair

Wet hair odor after treatment was compared for invention vs. control. The results are described in Table 1F.

TABLE 1F

Comparison of the wet hair odor between Uberliss Smoothing Treatment containing 15.00% Glyoxylic Acid and composition containing Silmer® NH Di-8 and 11.25% Glyxoylic Acid

| Model No. | Control System (Uberliss®) Odor Score | Invention (Formulae 1A-1 and 1B-1) Odor Score |
|---|---|---|
| 1 | 4.00 | 5.00 |
| 2 | 4.00 | 5.00 |
| 3 | 4.00 | 5.00 |
| 4 | 4.00 | 5.00 |
| 5 | 4.00 | 5.00 |

The average score of no odor is 4.0 for the control group and 5.0 for the group treated with the composition of the invention. The composition of the invention produced significantly less undesirable odor following treatment relative to control.

The results demonstrate that when a micro emulsion of an aminosilicone, e.g., Silmer® NH Di-8, is applied to hair followed by reduced concentrations of glyoxylic acid (10-11.5%), the wavy/curly hair becomes equally straight, is as easy or easier to comb, has less static charge, and has less undesirable odor relative to conventional treatments with 15.0% glyoxylic acid concentrations.

Example 2

This example demonstrates compositions and methods of the present invention.

Fiber Expander and Fiber Restructure compositions are described below in Tables 2A and 2B.

TABLE 2A

Fiber Expander Formulae

| Ingredients | 2A-1 % | 2A-2 % | 2A-3 % | 2A-4 % | 2A-5 % | 2A-6 % | 2A-7 % | 2A-8 % | 2A-9 % |
|---|---|---|---|---|---|---|---|---|---|
| Deionized Water | 91.50 | 92.44 | 91.50 | 90.00 | 89.00 | 89.00 | 90.25 | 92.50 | 92.50 |
| Silmer ® NH Di-8 | 2.50 | 1.56 | 1.25 | 2.50 | 1.25 | 1.25 | 1.25 | | 0.00 |
| Silmer ® NH Di-50 | | | | | | | | 1.50 | 0.00 |
| Silmer ® NH C-50 | | | | | | | | | 1.50 |
| Silmer ® EP Di-10 | | | 0.75 | 1.50 | 0.00 | 2.50 | 0.00 | | 0.00 |
| Silmer ® EP J2 | | | 0.00 | 0.00 | 1.25 | 0.00 | 2.50 | | 0.00 |
| Silube D 208-1 AGE | | | | | | | | | 0.00 |
| Lipocol L-23 | 4.00 | 4.00 | 4.000 | 4.00 | 4.00 | 4.00 | 4.00 | 4.00 | 6.00 |
| Fragrance | 2.00 | 2.00 | 2.000 | 2.00 | 2.00 | 2.00 | 2.00 | 2.00 | 3.00 |

TABLE 2B

Fiber Restructure Formulae

| Ingredients | 2B-1 % | 2B-2 % | 2B-3 % |
|---|---|---|---|
| Deionized Water | 69.50 | 72.000 | 71.220 |
| Lipocol L-23 | 6.00 | 6.000 | 6.000 |
| Fragrance | 2.00 | 2.000 | 2.000 |
| Silmer ® EP J2 | | 0.000 | 0.780 |
| Glyoxylic Acid (50% active) | 22.50 | 20.00 | 20.000 | pH @ 25 C. = 1.81

Combination of Silmer® NH Di-8 (1.25%), Silmer® EP Di-10 (0.75%) and Glyoxylic Acid at 10.0% Active A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill., USA. The application procedure is given below.

Application Procedure—Control
See Example 1, except that no KeraCare Thermal Wonder Thermal Protect was applied to hair.

Application Procedure—Invention
Divide hair into two halves.
Shampoo hair once using Uberliss® Hydrating Shampoo.
Apply Experimental Expander (Formula 2A-3, Table 2A) by using 15 to 20 strokes or 10 to 15 g per half head.
Dry hair to 80%.
Apply 20 to 25 g of Experimental Fiber Restructure (Formula 2B-2, Table 2B) using a brush and combing through the hair.
Cover hair with plastic or Aluminum Cap. Leave product on hair for 30 minutes under dryer or steamer at high setting. Remove cap.
Allow the hair to cool down for 5 minutes.
Rinse hair for 10 seconds with low pressure tepid water. The rinse water will be still whitish or like Coco-water.
Blow dry hair completely using paddle brush.
Divide hair into thin partings and flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Comparison of Hair Straightening
The comparison of wet hair straighten after treatment was conducted and the results are shown in Table 2C.

TABLE 2C

The comparison of the wet hair straightening between Uberliss Smoothing Treatment containing 15.00% Glyoxylic Acid and Experimental Treatment with Silmer ® NH Di-8, Silmer ® EP Di-10 and 10.00% Glyoxylic Acid

| Model No. | Control System (Uberliss ®) Straightening Score | Invention (Formulae 2A-3 and 2B-2) Straightening Score |
|---|---|---|
| 1 | 5.0 | 4.5 |
| 2 | 5.0 | 5.0 |
| 3 | 4.0 | 5.0 |
| 4 | 4.5 | 5.0 |
| 5 | 4.8 | 5.0 |

The group treated according to the invention exhibited a higher straightening score of 4.90 as compared to the control group score of 4.60. The group treated according to the invention was treated with only 10.0% of Glyoxylic Acid as compared to the control group that was treated with significantly higher concentrations of 15.0% Glyoxylic Acid. The invention provides for lower levels of Glyoxylic Acid without loss of efficacy in straightening hair.

Comparison of Hair Combing
The comparison of wet combing of hair was conducted after the treatment process and the results are shown in Table 2D.

TABLE 2D

The comparison of the wet hair combing between Uberliss Smoothing Treatment containing 15.00% Glyoxylic Acid and Experimental Treatment with Silmer ® NH Di-8, Silmer ® EP Di-10 and 10.00% Glyxoylic Acid

| Model No. | Control System (Uberliss ®) Wet combing score | Invention (Formulae 2A-3 and 2B-2) Wet combing score |
|---|---|---|
| 1 | 5.0 | 5.0 |
| 2 | 5.0 | 5.0 |
| 3 | 3.9 | 4.0 |
| 4 | 5.0 | 5.0 |
| 5 | 4.0 | 4.0 |

The ease of wet combing score for the group treated with the composition of the invention was at least equal to the score exhibited by the control group.

Comparison of Static Charge
The comparison of static charge was conducted between the two groups using Static Charge Probe that measures charge in Kilo Volts (KV) after hair is combed repeatedly for 20 strokes. The scores of static charges in KV are shown in Table 2E.

TABLE 2E

The comparison of the static charge in Kilo Volts between control Uberliss Smoothing Treatment containing 15.00% Glyoxylic Acid and Experimental Treatment with Silmer® NH Di-8, Silmer® EP Di-10 and 10.00% Glyxoylic Acid

| Model No. | Control System (Uberliss®) static charge (KV) | Invention (Formulae 2A-3 and 2B-2) static charge (KV) |
|---|---|---|
| 1 | 8.11 | 2.4 |
| 2 | 19.05 | 11.08 |
| 3 | 16.1 | 1.5 |
| 4 | 9.05 | 3.5 |
| 5 | 9.80 | 5.32 |

The control group has a mean static charge of 12.40 KV while the experimental group has a mean static charge of 4.76 KV. The experimental group has significantly less static charge on hair than the control group, at p=0.014, p<0.05. Since the static charge is significantly less on the hair that is treated with Silmer® NH Di-8 and Silmer® EP Di-10, hair is more manageable and stylable.

Comparison of Odor in Wet Hair after the Treatment

The comparison of hair odor after treatment was conducted between the two groups using nose/smell test by the hairstylists and smell was assessed on a scale of 1 to 5, where 5 was no odor and 1 was very unpleasant odor. The scores of wet hair odor are shown in Table 2F.

TABLE 2F

The comparison of the odor between control Uberliss Smoothing Treatment containing 15.00% Glyoxylic Acid and Experimental Treatment with Silmer® NH Di-8, Silmer® EP Di-10 and 10.00% Glyxoylic Acid

| Model No. | Control System (Uberliss®) hair odor | Invention (Formulae 2A-3 and 2B-2) hair odor |
|---|---|---|
| 1 | 3.90 | 4.50 |
| 2 | 3.80 | 4.60 |
| 3 | 3.70 | 4.40 |
| 4 | 3.85 | 4.70 |
| 5 | 4.00 | 4.85 |

The odor likability for the control group is 3.85 whereas the odor likability of the experimental group is 4.61. The experimental group score of 4.61 is significantly better than the control group.

Combination of Silmer® NH Di-8 (2.50%) and Silmer® EP Di-10 (1.50%) and Glyoxylic Acid at 10.0% Active A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill., USA. The application procedure is given below.

Application Procedure for Control Products Regimen:
  Divide hair into two halves.
  Shampoo hair once using Uberliss® Hydrating Shampoo.
  Apply Uberliss® Expander by using 15 to 20 strokes or 10 to 15 g per half head.
  Dry hair to 80%.
  Apply 20 to 25 g of Uberliss Fiber Restructure using a brush and combing through the hair.
  Cover hair with plastic or Aluminum Cap. Leave product on hair for 30 minutes under dryer or steamer at high setting. Remove cap.
  Allow the hair to cool down for 5 minutes.
  Rinse hair for 10 seconds with low pressure tepid water. The rinse water will be still whitish or like Coco-water.
  Blow dry hair completely using paddle brush.
  Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
  After straightening, wet a section of hair to compare and evaluate the hair straightening between the two halves of head.

Application Procedure for Experimental Products Regimen:
  Divide hair into two halves.
  Shampoo hair once using Uberliss® Hydrating Shampoo.
  Apply Experimental Expander (Formula 2A-4, Table 2A) by using 15 to 20 strokes or 10 to 15 g per half head.
  Dry hair to 80%.
  Apply 20 to 25 g of Experimental Fiber Restructure (Formula 2B-2, Table 2B) using a brush and combing through the hair.
  Cover hair with plastic or Aluminum Cap. Leave product on hair for 30 minutes under dryer or steamer at high setting. Remove cap.
  Allow hair to cool down for 5 minutes.
  Rinse hair for 10 seconds with low pressure tepid water. The rinse water will be still whitish or like Coco-water.
  Blow dry hair completely using paddle brush.
  Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
  After straightening, wet a section of hair to compare and evaluate the hair straightening and hair odor between the two halves of head.

Comparison of Hair Straightening

The comparison of wet hair straighten after treatment was conducted and the results are shown in Table 2G.

TABLE 2G

The comparison of the wet hair straightening between Uberliss Smoothing Treatment containing 15.00% Glyoxylic Acid and Experimental Treatment with Silmer® NH Di-8 (2.5%), Silmer® EP Di-10 (1.50%) and 10.00% Glyxoylic Acid

| Model No. | Control System (Uberliss®) Straightening Score | Invention (Formulae 2A-4 and 2B-2) Straightening Score |
|---|---|---|
| 1 | 5.00 | 4.90 |
| 2 | 5.00 | 5.00 |
| 3 | 4.90 | 4.70 |

The results of the salon testing show a clear difference in the two sides. The control side had better straightening, therefore, testing was halted after three half heads study.

Combination of Silmer® NH Di-8 (1.25%) and Silmer® EP J2 (1.25%) and Glyoxylic Acid at 10.0% Active A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill. 60160, USA. The application procedure is given below.

Application Procedure for Control Products Regimen:
Divide hair into two halves.
Shampoo hair once using Uberliss® Hydrating Shampoo.
Apply Uberliss® Expander by using 15 to 20 strokes or 10 to 15 g per half head.
Dry hair to 80%.
Apply 20 to 25 g of Uberliss Fiber Restructure using a brush and combing through the hair.
Cover hair with plastic or Aluminum Cap. Leave product on hair for 30 minutes under dryer or steamer at high setting. Remove cap.
Allow the hair to cool down for 5 minutes.
Rinse hair for 10 seconds with low pressure tepid water. The rinse water will be still whitish or like Coco-water.
Blow dry hair completely using paddle brush.
Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
After straightening, wet a section of hair to compare and evaluate the hair straightening between the two halves of head.

Application Procedure for Experimental Products Regimen:
Divide hair into two halves.
Shampoo hair once using Uberliss® Hydrating Shampoo.
Apply Experimental Expander (Formula 2A-5, Table 2A) by using 15 to 20 strokes or 10 to 15 g per half head.
Dry hair to 80%.
Apply 20 to 25 g of Experimental Fiber Restructure (Formula 2B-2, Table 2B) using a brush and combing through the hair.
Cover hair with plastic or Aluminum Cap. Leave product on hair for 30 minutes under dryer or steamer at high setting. Remove cap.
Allow hair to cool down for 5 minutes.
Rinse hair for 10 seconds with low pressure tepid water. The rinse water will be still whitish or like Coco-water.
Blow dry hair completely using paddle brush.
Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
After straightening, wet a section of hair to compare and evaluate the hair straightening and hair odor between the two halves of head.

Comparison of Hair Straightening

The comparison of wet hair straighten after treatment was conducted and the results are shown in Table 2H.

TABLE 2H

The comparison of the wet hair straightening between Uberliss Smoothing Treatment containing 15.00% Glyoxylic Acid and Experimental Treatment with Silmer® NH Di-8 (1.25%), Silmer® EP J2 (1.25%) and 10.00% Glyoxylic Acid

| Model No. | Control System (Uberliss ®) Straightening Score | Invention (Formulae 2A-5 and 2B-2) Straightening Score |
|---|---|---|
| 1 | 3.70 | 4.50 |
| 2 | 4.00 | 4.50 |
| 3 | 3.70 | 4.50 |
| 4 | 4.90 | 4.00 |
| 5 | 3.00 | 5.00 |

The average score of straightening for control group is 3.86 while the average straightening score of the group treated according to the invention is 4.50. The combination of Silmer® NH Di-8, Silmer® EP J2 and 10.0% Glyoxylic Acid did not result in any loss in straightening efficacy relative to the control containing 15.0% Glyoxylic Acid. This is a significant improvement as the invention provides significant benefits such as, e.g., excellent wet combing, less static charge, and less unpleasant odor as compared to conventional products, but without sacrificing straightening efficacy.

Comparison of Hair Combing

The comparison of wet combing of hair was conducted after the treatment process and the results are shown in Table 2I.

TABLE 2I

The comparison of the wet hair combing between Uberliss Smoothing Treatment containing 15.00% Glyoxylic Acid and Experimental Treatment with Silmer® NH Di-8, Silmer® EP Di-10 and 10.00% Glyoxylic Acid

| Model No. | Control System (Uberliss ®) Wet combing score | Invention (Formulae 2A-5 and 2B-2) Wet combing score |
|---|---|---|
| 1 | 5.00 | 5.00 |
| 2 | 3.50 | 4.00 |
| 3 | 4.00 | 5.00 |
| 4 | 3.70 | 5.00 |
| 5 | 5.00 | 5.00 |

The ease of wet combing score for control group is 4.24 and group treated according to the invention is 4.80. The composition of the invention results in fibers that are easier to comb, as compared to control, and the difference is perceivable by the hair stylists.

Comparison of Static Charge

The comparison of static charge was conducted between the two groups using Static Charge Probe that measures charge in Kilo Volts (KV) after hair is combed repeatedly for 20 strokes. The scores of static charges in KV are shown in Table 2J.

TABLE 2J

The comparison of the static charge in Kilo Volts between control Uberliss Smoothing Treatment containing 15.00% Glyoxylic Acid and Experimental Treatment with Silmer® NH Di-8 (1.25%), Silmer® EP J2 (1.25%) and 10.00% Glyoxylic Acid

| Model No. | Control System (Uberliss ®) static charge (KV) | Invention (Formulae 2A-5 and 2B-2) static charge (KV) |
|---|---|---|
| 1 | 20.00 | 0.87 |
| 2 | 15.25 | −15.48 |
| 3 | −9.50 | −20.26 |

TABLE 2J-continued

The comparison of the static charge in Kilo Volts between control Uberliss Smoothing Treatment containing 15.00% Glyoxylic Acid and Experimental Treatment with Silmer ® NH Di-8 (1.25%), Silmer® EP J2 (1.25%) and 10.00% Glyxoylic Acid

| Model No. | Control System (Uberliss ®) static charge (KV) | Invention (Formulae 2A-5 and 2B-2) static charge (KV) |
|---|---|---|
| 4 | No reading Taken | No reading taken |
| 5 | 1.6 | 0.49 |

The average static charge on the control group is 6.8375 KV while the average static charge on group treated according to the invention is −8.595 KV. The difference in static charge is perceivable by the hair stylists.

Comparison of Odor in Wet Hair after the Treatment

The comparison of hair odor after treatment was conducted between the two groups using nose/smell test by the hairstylists and smell was assessed on a scale of 1 to 5, where 5 was no odor and 1 was very unpleasant odor. The scores of hair odor in wet stage are shown in Table 2K.

TABLE 2K

The comparison of the odor between control Uberliss Smoothing Treatment containing 15.00% Glyoxylic Acid and Experimental Treatment with Silmer ® NH Di-8, Silmer ® EP J2 and 10.00% Glyxoylic Acid

| Model No. | Control System (Uberliss ®) hair odor | Invention (Formulae 2A-5 and 2B-2) hair odor |
|---|---|---|
| 1 | 3.70 | 5.00 |
| 2 | 4.00 | 4.00 |
| 3 | 3.70 | 5.00 |
| 4 | 3.00 | 5.00 |
| 5 | 3.00 | 5.00 |

The control group has a mean score of 3.48 while the experimental group has a mean score of 4.8. The group treated according to the invention containing 10.0% Glyoxylic Acid has significantly less bad odor in the hair than the control group conventionally treated with a composition containing 15.0% Glyoxylic Acid.

Combination of Silmer® NH Di-8 (1.25%) and Silmer® EP J2 (2.50%) and Glyoxylic Acid at 10.0% Active A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill., USA. The application procedure is given below.

Application Procedure for Control products regimen:

Divide hair into two halves.

Shampoo hair once using Uberliss® Hydrating Shampoo.

Apply Uberliss® Expander by using 15 to 20 strokes or 10 to 15 g per half head.

Dry hair to 80%.

Apply 20 to 25 g of Uberliss Fiber Restructure using a brush and combing through the hair.

Cover hair with plastic or Aluminum Cap. Leave product on hair for 30 minutes under dryer or steamer at high setting. Remove cap.

Allow the hair to cool down for 5 minutes.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Application Procedure for Experimental Products Regimen:

Divide hair into two halves.

Shampoo hair once using Uberliss® Hydrating Shampoo.

Apply Experimental Expander (Formula 2A-7, Table 2A) by using 15 to 20 strokes or 10 to 15 g per half head.

Dry hair to 80%.

Apply 20 to 25 g of Experimental Fiber Restructure (Formula 2B-2, Table 2-B) using a brush and combing through the hair.

Cover hair with plastic or Aluminum Cap. Leave product on hair for 30 minutes under dryer or steamer at high setting. Remove cap.

Allow hair to cool down for 5 minutes.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening and hair odor between the two halves of head.

Comparison of Hair Straightening

The comparison of wet hair straighten after treatment was conducted and the results are shown in Table 2L.

TABLE 2L

The comparison of the wet hair straightening between Uberliss Smoothing Treatment containing 15.00% Glyoxylic Acid and Experimental Treatment with Silmer ® NH Di-8 (1.25%), Silmer ® EP J2 (2.50%) and 10.00% Glyxoylic Acid

| Model No. | Control System (Uberliss ®) Straightening Score | Invention (Formulae 2A-7 and 2B-2) Straightening Score |
|---|---|---|
| 1 | 4.00 | 5.00 |
| 2 | 3.00 | 4.50 |
| 3 | 5.00 | 5.00 |
| 4 | 4.00 | 3.00 |
| 5 | 3.00 | 3.5 |

The average score of straightening for control group is 3.80 while the average straightening score of the experimental group is 4.20.

Comparison of Hair Combing

The comparison of wet combing of hair was conducted after the treatment process and the results are shown in Table 2M.

TABLE 2M

The comparison of the wet hair combing between Uberliss Smoothing Treatment containing 15.00% Glyoxylic Acid and Experimental Treatment with Silmer ® NH Di-8, Silmer ® EP Di-10 and 10.00% Glyxoylic Acid

| Model No. | Control System (Uberliss ®) Wet combing score | Invention (Formulae 2A-7 and 2B-2) Wet combing score |
|---|---|---|
| 1 | 4.50 | 5.00 |
| 2 | 4.60 | 5.00 |
| 3 | 2.80 | 3.90 |
| 4 | 5.00 | 5.00 |
| 5 | 3.00 | 4.00 |

The ease of wet combing score for control group is 3.98 and experimental group is 4.58. For the group treated according to the invention, the fibers are easier to comb during wet stage as compare to the control system, and the difference is perceivable by the hair stylists.

Comparison of Static Charge

The comparison of static charge was conducted between the two groups using Static Charge Probe that measures charge in Kilo Volts (KV) after hair is combed repeatedly for 20 strokes. The scores of static charges in KV are shown in Table 2N.

TABLE 2N

The comparison of the static charge in Kilo Volts between control Uberliss Smoothing Treatment containing 15.00% Glyoxylic Acid and Experimental Treatment with Silmer ® NH Di-8 (1.25%), Silmer ® EP J2 (2.50%) and 10.00% Glyxoylic Acid

| Model No. | Control System (Uberliss ®) static charge (KV) | Invention (Formulae 2A-7 and 2B-2) static charge (KV) |
|---|---|---|
| 1 | 10.2 | 12.87 |
| 2 | 8.84 | 3.98 |
| 3 | 7.09 | 0.31 |
| 4 | 0.23 | 14.18 |
| 5 | 10.13 | 2.63 |

The average static charge on control group is 7.298 KV while the average static charge on Experimental group is 6.94 KV. The difference in static charge is perceivable by the hair stylists.

Comparison of Odor in Wet Hair after the Treatment

The comparison of hair odor after treatment was conducted between the two groups using nose/smell test by the hairstylists and smell was assessed on a scale of 1 to 5, where 5 was no odor and 1 was very unpleasant odor. The scores of odor in wet hair are shown in Table 2P.

TABLE 2P

The comparison of the odor between control Uberliss Smoothing Treatment containing 15.00% Glyoxylic Acid and Experimental Treatment with Silmer ® NH Di-8, Silmer ® EP J2 (252-75 J) and 10.00% Glyxoylic Acid

| Model No. | Control System (Uberliss ®) hair odor | Invention (Formulae 2A-7 and 2B-2) hair odor |
|---|---|---|
| 1 | 3.50 | 5.00 |
| 2 | 4.60 | 5.00 |
| 3 | 3.00 | 5.00 |
| 4 | 3.00 | 5.00 |
| 5 | 3.00 | 5.00 |

The control group has a mean score of 3.42 while the group treated according to the invention has a mean score of 5.00. The group treated according to the invention has significantly less bad odor in hair than the control group.

Combination of Silmer® NH Di-50 (1.50%) and Glyoxylic Acid at 10.0% Active

A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill. 60160, USA. The application procedure is given below.

Application Procedure for Control Products Regimen:

Divide hair into two halves.

Shampoo hair once using Uberliss® Hydrating Shampoo.

Apply Uberliss® Expander by using 15 to 20 strokes or 10 to 15 g per half head.

Dry hair to 80%.

Apply 20 to 25 g of Uberliss Fiber Restructure using a brush and combing through the hair.

Cover hair with plastic or Aluminum Cap. Leave product on hair for 30 minutes under dryer or steamer at high setting. Remove cap.

Allow the hair to cool down for 5 minutes.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Application Procedure for Experimental Products Regimen:

Divide hair into two halves.

Shampoo hair once using Uberliss® Hydrating Shampoo.

Apply Experimental Expander (Formula 2A-8, Table 2A) by using 15 to 20 strokes or 10 to 15 g per half head.

Dry hair to 80%.

Apply 20 to 25 g of Experimental Fiber Restructure (Formula 2B-2, Table 2B) using a brush and combing through the hair.

Cover hair with plastic or Aluminum Cap. Leave product on hair for 30 minutes under dryer or steamer at high setting. Remove cap.

Allow hair to cool down for 5 minutes.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening and hair odor between the two halves of head.

Comparison of Hair Straightening:

The comparison of wet hair straighten after treatment was conducted and the results are shown in Table 2Q.

TABLE 2Q

The comparison of the wet hair straightening between Uberliss Smoothing Treatment containing 15.00% Glyoxylic Acid and Experimental Treatment with Silmer ® NH Di-50 (1.50%) and 10.00% Glyoxylic Acid

| Model No. | Control System (Uberliss ®) Straightening Score | Invention (Formulae 2A-8 and 2B-2) Straightening Score |
|---|---|---|
| 1 | 4.7 | 4.9 |
| 2 | 4.0 | 4.0 |

The average score of straightening for control group is 4.35 while the average straightening score of the group treated according to the invention is 4.45. The composition of the invention straightens hair at least as effectively as the composition used in the control group.

Combination of Silmer® NH Di-8 (1.56%) as an Expander and Glyoxylic Acid at 10.0% Active with Silmer® EP J2 at 0.78%

A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill. 60160, USA. The application procedure is given below.

Application Procedure for Control Products Regimen:
Divide hair into two halves.
Shampoo hair once using Uberliss® Hydrating Shampoo.
Apply Uberliss® Expander by using 15 to 20 strokes or 10 to 15 g per half head.
Dry hair to 80%.
Apply 20 to 25 g of Uberliss Fiber Restructure using a brush and combing through the hair.
Cover hair with plastic or Aluminum Cap. Leave product on hair for 30 minutes under dryer or steamer at high setting. Remove cap.
Allow the hair to cool down for 5 minutes.
Rinse hair for 10 seconds with low pressure tepid water. The rinse water will be still whitish or like Coco-water.
Blow dry hair completely using paddle brush.
Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
After straightening, wet a section of hair to compare and evaluate the hair straightening between the two halves of head.

Application Procedure for Experimental Products Regimen:
Divide hair into two halves.
Shampoo hair once using Uberliss® Hydrating Shampoo.
Apply Experimental Expander (Formula 2A-2, Table 2A) by using 15 to 20 strokes or 10 to 15 g per half head.
Dry hair to 80%.
Apply 20 to 25 g of Experimental Fiber Restructure (Formula 2B-3, Table 2B) using a brush and combing through the hair.
Cover hair with plastic or Aluminum Cap. Leave product on hair for 30 minutes under dryer or steamer at high setting. Remove cap.
Allow hair to cool down for 5 minutes.
Rinse hair for 10 seconds with low pressure tepid water. The rinse water will be still whitish or like Coco-water.
Blow dry hair completely using paddle brush.
Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.
After straightening, wet a section of hair to compare and evaluate the hair straightening and hair odor between the two halves of head.

Comparison of Hair Straightening

The comparison of wet hair straighten after treatment was conducted and the results are shown in Table 2R.

TABLE 2R

The comparison of the wet hair straightening between Uberliss Smoothing Treatment containing 15.00% Glyoxylic Acid and Experimental Treatment with Silmer ® NH Di-8 (1.56%), and a mixture of 10.00% Glyoxylic Acid and Silmer ® EP J2 (0.78%)

| Model No. | Control System (Uberliss ®) Straightening Score | Invention (Formulae 2A-2 and 2B-3) Straightening Score |
|---|---|---|
| 1 | 3.50 | 4.50 |
| 2 | 3.50 | 3.00 |
| 3 | 4.60 | 4.50 |
| 4 | 4.00 | 4.00 |
| 5 | 4.90 | 4.80 |

The average score of straightening for control group is 4.10 while the average straightening score of the experimental group is 4.16. The composition of the invention straightens hair at least as effectively as the composition used in the control group.

Comparison of Hair Combing

The comparison of wet combing of hair was conducted after the treatment process and the results are shown in Table 2S.

TABLE 2S

The comparison of the wet hair combing between Uberliss Smoothing Treatment containing 15.00% Glyoxylic Acid and Experimental Treatment with Silmer ® NH Di-8 (1.56%), and a mixture of 10.00% Glyoxylic Acid and Silmer ® EP J2 (0.78%)

| Model No. | Control System (Uberliss ®) Wet combing score | Invention (Formulae 2A-2 and 2B-3) Wet combing score |
|---|---|---|
| 1 | 3.00 | 5.00 |
| 2 | 3.00 | 5.00 |
| 3 | 3.00 | 5.00 |
| 4 | 4.00 | 5.00 |
| 5 | 4.00 | 5.00 |

The mean score of control group wet combing is 3.40 and the mean score for the group treated according to the invention is 5.00. Therefore, it is inferred that the experimental group makes the fibers easier to comb during wet stage as compare to the control system. The difference is perceivable by the hair stylists as well.

Comparison of Static Charge

The comparison of static charge was conducted between the two groups using Static Charge Probe that measures charge in Kilo Volts (KV) after hair is combed repeatedly for 20 strokes. The scores of static charges in KV are shown in Table 2T.

TABLE 2T

Comparison of static charge in Kilo Volts between control Uberliss Smoothing Treatment containing 15.00% Glyoxylic Acid and Experimental Treatment with Silmer ® NH Di-8 (1.56%), and a mixture of 10.00% Glyoxylic Acid and Silmer ® EP J2 (0.78%)

| Model No. | Control System (Uberliss ®) static charge (KV) | Invention (Formulae 2A-2 and 2B-3) static charge (KV) |
|---|---|---|
| 1 | 4.24 | 2.47 |
| 2 | 7.42 | 4.76 |
| 3 | 3.60 | 0.25 |

The average static charge on control group is 5.067 KV while the average static charge on group treated according to the invention is 2.493 KV. The difference in static charge is significant and perceivable by the hair stylists.

Comparison of Odor in Wet Hair after the Treatment

The comparison of hair odor after treatment was conducted between the two groups using nose/smell test by the hairstylists and smell was assessed on a scale of 1 to 5, where 5 was no odor and 1 was very unpleasant odor. The scores of odor in wet hair are shown in Table 2U.

TABLE 2U

The comparison of the odor between control Uberliss Smoothing Treatment containing 15.00% Glyoxylic Acid and Experimental Treatment with Silmer ® NH Di-8, and 10.00% Glyoxylic Acid and Silmer ® EP J2 (0.78%)

| Model No. | Control System (Uberliss ®) hair odor | Invention (Formulae 2A-2 and 2B-3) hair odor |
|---|---|---|
| 1 | 3.00 | 4.70 |
| 2 | 3.00 | 4.60 |
| 3 | 4.00 | 4.80 |
| 4 | 3.00 | 4.95 |
| 5 | 3.00 | 5.00 |

The control group has a mean score of 3.20 while the group treated according to the invention has a mean score of 4.81. The experimental group has significantly less bad odor in hair than the control group.

When a micro-emulsion containing an aminosilicone, e.g., Silmer® NH Di-8, and an epoxysilicone, e.g., Silmer® EP Di-10, is applied followed by reduced concentrations of Glyoxylic Acid, the wavy/curly hair becomes equally straight, easier to comb, has less static charge, and has less undesirable odor, as compared to hair treated with conventional compositions containing 15.0% glyoxylic acid.

Example 3

This example demonstrates compositions and methods of the present invention.

Combination of Silmer® NH C50 and Glyoxylic Acid

A survey questionnaire as in Examples 1 and 2 was used to record the data in hair smoothing treatments by a trained hairstylist who performed the treatment at the time of products' application and process. Five individuals were treated with Fiber Expander containing Silmer® NH C 50 followed by the Fiber Restructure containing a reduced concentration of Glyoxylic Acid (10.0%).

A head of human hair was divided into two halves from the middle of the forehead to the back of the head. One side of the hair was treated with a commercial product system which contains 15.00% active Glyoxylic Acid. This system is marketed under the trade name of Uberliss® Smoothing Treatment by Salon Commodities® of Melrose Park, Ill., USA. The Application Procedure is Given Below.

Application Procedure—Control

Divide hair into two halves.

Shampoo hair once using Uberliss® Hydrating Shampoo.

Apply Uberliss® Expander by using 15 to 20 strokes or 10 to 15 g per half head.

Dry hair to 80%.

Apply 20 to 25 g of Uberliss Fiber Restructure using a brush and combing through the hair.

Cover hair with plastic or Aluminum Cap. Leave product on hair for 20 minutes under dryer or steamer at high setting. Remove cap.

Apply ¼ tea spoon of Uberliss Nutritive Mask. Comb through using wide-tooth comb and cover hair with plastic or Aluminum Cap. Leave the product on for 10 minutes under the hooded dryer or steamer.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Application Procedure—Invention

Divide hair into two halves.

Shampoo hair once using Uberliss® Hydrating Shampoo.

Apply Experimental Expander (Formula 2A-9, Table 2A) by using 15 to 20 strokes or 10 to 15 g per half head.

Dry hair to 80%.

Apply 20 to 25 g of Experimental Fiber Restructure (Formula 2B-2, Table 2B) using a brush and combing through the hair.

Cover hair with plastic or Aluminum Cap. Leave product on hair for 30 minutes under dryer or steamer at high setting. Remove cap.

Rinse hair for 10 seconds with low pressure tepid water. The rinse water will be still whitish or like Coco-water.

Blow dry hair completely using paddle brush.

Divide hair into thin partings. Flat iron hair with three partial strokes near the roots of hair, followed by 7 complete stokes throughout the hair shaft. The temperature of the flat iron should be set between 375° to 450° F. Higher temperature imparts greater straightening.

After straightening, wet a section of hair to compare and evaluate the hair straightening between the two halves of head.

Also evaluate and compare hair odor, and static charge on the hair.

Comparison of Hair Straightening

Wet hair straightening after treatment was compared. The results are shown in Table 3A.

TABLE 3A

The comparison of the wet hair straightening between Uberliss Smoothing Treatment containing 15.00% Glyoxylic Acid and Experimental Treatment with Silmer ® NH C 50 (1.50%) and 10.00% Glyxoylic Acid

| Model No. | Control System (Uberliss ®) Straightening Score | Invention (Formulae 2A-9 and 2B-2) Straightening Score |
|---|---|---|
| 1 | 4.00 | 5.00 |
| 2 | 4.50 | 4.50 |
| 3 | 4.00 | 3.70 |
| 4 | 4.50 | 4.00 |
| 5 | 4.00 | 4.90 |
| 6 | 4.40 | 5.00 |

The average of straightening ability of control group is 4.2333 as compare to the average straighten ability of 4.5167 for the experimental group. The experimental group containing 10.00% Glyoxylic Acid and 1.50% of Silmer® NH C 50 (252-75 O) impart somewhat better degree of straightening to wavy/curly hair as compare to 15.00% Glyxoylic Acid (Uberliss Fiber Restructure). There is no difference in the hair straightening of 10.00% Glyxoylic Acid and Silmer® NH C50 as compared to 15.00% Glyoxylic Acid.

Comparison of Combing

A comparison of ease of wet combing between control and experimental groups was conducted and the results are shown in Table 3B.

TABLE 3B

The comparison of the wet hair combing between Uberliss Smoothing Treatment containing 15.00% Glyoxylic Acid and Experimental Treatment with Silmer ® NH C50 and 10.0% Glyxoylic Acid

| Model No. | Control System (Uberliss ®) Ease of wet combing Score | Invention (Formulae 2A-9 and 2B-2) Ease of wet combing Score |
|---|---|---|
| 1 | 4.70 | 5.00 |
| 2 | 3.80 | 4.00 |
| 3 | 1.00 | 5.00 |
| 4 | 3.50 | 5.00 |
| 5 | 4.00 | 5.00 |
| 6 | 4.00 | 5.00 |

The average wet ease of combing for control group is 3.50 and the experimental group is 4.8333, which is better than the control. The addition of Silmer® NH C50 with Glyoxylic Acid helps make hair fibers easier to comb during wet state.

Comparison of Static Charge

The comparison of hair static charge between control and experimental groups was conducted and the results are shown in Table 3C.

TABLE 3C

The comparison of the static charge between Uberliss Smoothing Treatment containing 15.00% Glyoxylic Acid and Experimental Treatment with Silmer ® NH C 50 and 10.00% Glyxoylic Acid

| Model No. | Control System (Uberliss ®) Degree of static charge | Invention (Formulae 2A-9 and 2B-2) Degree of static charge |
|---|---|---|
| 1 | 5.00 | 5.00 |
| 2 | 3.00 | 4.50 |

TABLE 3C-continued

The comparison of the static charge between Uberliss Smoothing Treatment containing 15.00% Glyoxylic Acid and Experimental Treatment with Silmer ® NH C 50 and 10.00% Glyxoylic Acid

| Model No. | Control System (Uberliss ®) Degree of static charge | Invention (Formulae 2A-9 and 2B-2) Degree of static charge |
|---|---|---|
| 3 | 5.00 | 5.00 |
| 4 | 5.00 | 4.50 |
| 5 | 5.00 | 5.00 |
| 6 | 2.00 | 5.00 |

The stylists' perception regarding no static charge on hair during flat ironing and combing is as follow:

Control group is 4.1667 and experimental group is 4.833. The stylists could perceive the difference and the experimental group showed less static charge during flat ironing and combing hair.

Comparison of Odor of Treated wet hair

A comparison of wet hair odor after treatment was conducted and the results are shown in Table 3D.

TABLE 3D

The comparison of the wet hair odor between Uberliss Smoothing Treatment containing 15.00% Glyoxylic Acid and Experimental Treatment with Silmer ® NH C 50 and 10.00% Glyxoylic Acid

| Model No. | Control System (Uberliss ®) Degree of no odor in wet hair | Invention (Formulae 2A-9 and 2B-2) Degree of no odor in wet hair |
|---|---|---|
| 1 | 3.50 | 5.00 |
| 2 | 3.00 | 5.00 |
| 3 | 2.00 | 5.00 |
| 4 | 4.00 | 5.00 |
| 5 | 3.00 | 5.00 |
| 6 | 3.00 | 5.00 |

The no odor score for control group is 3.0833 and experimental group is 5.00. The experimental group has no odor in wet hair as compare to control group.

When a micro emulsion of a compound of formula (I) is applied to hair followed by a reduced concentration of glyoxylic acid (10.0%), wavy/curly hair becomes equally straight, easier to comb, has less static charge, and less odor as compared to wavy/curly hair conventionally treated with glyoxylic acid at a 15.0% concentration.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for straightening hair, the method comprising contacting the hair with a hair straightening agent which is a glyoxylic acid or salt thereof at a concentration of about 10-11.5% and an effective amount of a compound of the formula:

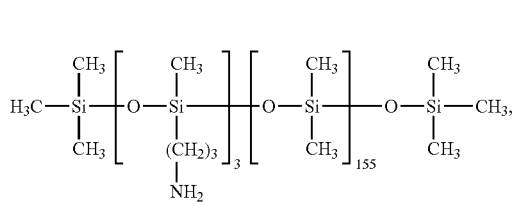

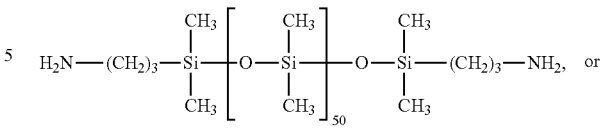

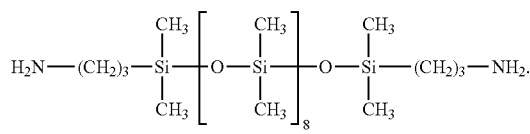

applying heat to the hair at a temperature of from about 375° F. to about 450° F., and straightening the hair.

2. The method of claim 1, wherein the glyoxylic acid or salt thereof is applied at a glyoxylic acid concentration of about 10%.

3. The method of claim 2, wherein the compound of formula I(a), I(b), or I(c) is applied to the hair before the hair straightening agent is applied to the hair.

4. The method of claim 3, wherein the compound of formula I(a), I(b), or I(c) and hair straightening agent are applied to the hair concurrently.

5. The method of claim 4, further comprising contacting the hair with an effective amount of an epoxysilicone.

6. The method of claim 5, wherein the epoxysilicone is of the formula:

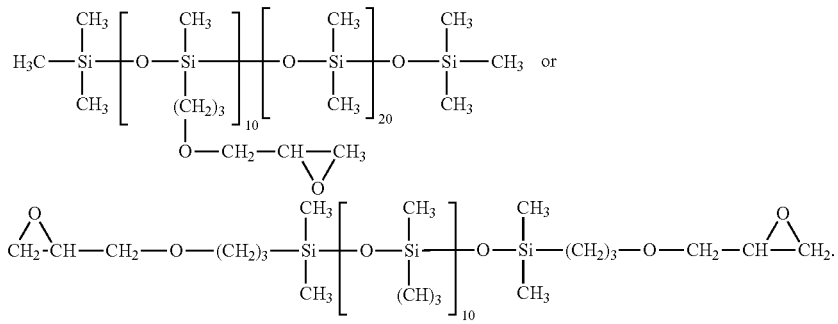

7. The method of claim 1, wherein the hair straightening is performed with a flat iron.

8. The method of claim 1, wherein the compound of formula I(a), I(b), or I(c) is:

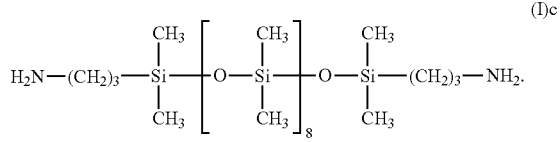

* * * * *